United States Patent
Ghabra et al.

(10) Patent No.: US 10,905,543 B2
(45) Date of Patent: Feb. 2, 2021

(54) INTRA CORNEAL IMPLANTS AND METHODS OF USING SAME

(71) Applicant: MAG OPTICS, LTD., London (GB)

(72) Inventors: Marwan Ghabra, London (GB); Hakam Ghabra, London (GB)

(73) Assignee: MAG OPTICS, LTD., London (GB)

( * ) Notice: Subject to any disclaimer, the term of this patent is extended or adjusted under 35 U.S.C. 154(b) by 310 days.

(21) Appl. No.: 15/610,434

(22) Filed: May 31, 2017

(65) Prior Publication Data
US 2017/0258576 A1 Sep. 14, 2017

Related U.S. Application Data

(63) Continuation of application No. PCT/IB2015/002463, filed on Dec. 1, 2015.
(60) Provisional application No. 62/085,736, filed on Dec. 1, 2014.

(51) Int. Cl.
*A61F 2/14* (2006.01)
(52) U.S. Cl.
CPC .............. *A61F 2/145* (2013.01); *A61F 2/147* (2013.01); *A61F 2230/0008* (2013.01); *A61F 2230/0019* (2013.01); *A61F 2250/006* (2013.01)
(58) Field of Classification Search
CPC ............. A61F 2/145; A61F 2/147; A61F 2/15
See application file for complete search history.

(56) References Cited

U.S. PATENT DOCUMENTS 7,476,398 B1    1/2009  Doillon et al. ............... 424/423

FOREIGN PATENT DOCUMENTS

| RU | 12348 | 1/2000 | A61F 9/00 |
|---|---|---|---|
| RU | 2428955 | 9/2011 | A61F 2/14 |
| WO | WO 95/03747 | 2/1995 | A61B 19/00 |
| WO | WO 95/03755 | 2/1995 | A61F 2/14 |
| WO | WO 96/40005 | 12/1996 | A61F 2/14 |
| WO | WO 01/17460 | 3/2001 | A61F 2/14 |
| WO | WO-0117460 A1 * | 3/2001 | A61F 9/00781 |
| WO | WO 09/158723 | 12/2009 | A61F 2/14 |

OTHER PUBLICATIONS

International Search Report for PCT Patent Application No. PCT/IB2015/002463 pp. 1-3 (dated May 19, 2016).
International Preliminary Report on Patentability, PCT Application No. PCT/IB2015/002463, pp. 1-5 (dated Jun. 6, 2017).
EP Extended Search Report and Search Opinion; EP 15865047.3, pp. 1-8 (dated Jun. 25, 2018).

* cited by examiner

Primary Examiner — Christopher D. Prone
Assistant Examiner — Christine L Nelson
(74) Attorney, Agent, or Firm — J. Peter Paredes; Rosenbaum IP, P.C.

(57) ABSTRACT

The present disclosure provides intra ocular implants and methods of using same to treat various refraction errors in a patient's eye.

20 Claims, 11 Drawing Sheets

INTRA CORNEAL IMPLANTS AND METHODS OF USING SAME

CROSS-REFERENCE TO RELATED APPLICATIONS

This application is a continuation of, and claims priority from, PCT Application Ser. No. PCT/162015/002463, filed Dec. 1, 2015, which claims the benefit of priority to U.S. Provisional Patent Application Ser. No. 62/085,736, filed Dec. 1, 2014, all of which the entire contents of which are incorporated herein by reference and relied upon.

FIELD

The present technology relates generally to corneal implants, including intrastromal/intracorneal inlays, and methods to adjust refraction by altering the curvature of the anterior and posterior surface of the cornea. The present technology also relates to corneal intrastromal radial incision patterns and methods of mapping a corneal intrastromal radial incision pattern specific to a subject's corneal topography.

BACKGROUND

Deviations from the normal shape and curvature of the corneal surface produce errors of refraction in the visual process. A variety of eye disorders such as myopia, hyperopia, keratoconus and astigmatism all are commonly known as refractive errors. Refractive errors all constitute alterations in the curvature and shape of the cornea.

For a hyperopic eye to focus light correctly onto the retina, it must either accommodate to increase the convexity of the physiological lens to compensate for the decreased angle of refraction. Alternatively a lens of contact lens of sufficient/adequate convexity can be added to assist in focusing light rays onto the cornea.

Correction of myopia includes placing a concave lens in front of the cornea, or to reduce the degree of steepness of the cornea by selectively flattening the cornea via the LASIK (Laser Assisted In Situ Keratomileusis) procedure.

Current correction of astigmatic error involves toric intraocular lenses (IOLs) with a meridian distribution that compliments the astigmatic cornea. Another version of correction is the more invasive inlay insertion of corneal rings created by Intacs, Ferrara Rings and Keravision, corneal rings which operate by exerting outward forces on the cornea in an attempt to stretch the steep meridian outward to create unity in the curvature of the meridians of the cornea. For astigmatic patients with cataracts, the toric intraocular lens can be used to replace the pseudo-aphakia induced by phacoemulsification, and the toric component of the lens can be correctly aligned to compliment the meridians of the astigmatic cornea.

Keratoconic correction involves both non-invasive contact lenses, hybrid lenses and scleral contact lenses and more invasive procedures such as corneal transplant, intra-stromal corneal rings designed to push out against the curvature of the cornea in an attempt to flatten the peak of the cone and return to a more natural shape.

There is a wide array of implants to attempt to correct presbyopia. Some methods involve creating a hyperbolic cornea by way of an insertion of an inlay. The hyperbolic cornea has a central area more convex than the remainder of the cornea, the significance of such a cornea is the increased refractive power centrally that shall be able to refract light rays from a near object falling on the central portion. Whereas the light from distant objects falls onto the peripheral cornea and shall be refracted accordingly as there is less refractive power needed to converge distant light rays. Acufocus however works by placing a thin inlay into the central cornea with a central opening that employs the pinhole effect extending the depth of focus. Acufocus have also deployed this concept onto the intra-ocular lens. Alcon, Bausch and Lomb, Abbot Medical Optics and Hoya among others intraocular lens manufacturer produce lenses with multi-focality. Either bifocal, trifocal or multifocal lenses are in essence different lenses with different optical power connected to each other. For example the multifocal IOL, the lens focuses light onto a range of focal points based on the corresponding section with a specific dioptre power within the lens. The result is a series of images that form on the retina to which the brain must neuroadapt to always correctly choose the most visually focused image.

Corneal arches and implants rely on the principle that a cornea will remodel when an inlay or onlay is applied to it. The cornea shall do this in an attempt to minimise the effects of the procedure. For example, Watksy et al. demonstrated the effect of inlays on the anterior corneal surface. The "Watsky Model" demonstrated that the new radius of curvature of the anterior cornea after implantation was directly influenced by the implants. However, this effect seems to be most applicable in inlays having a thickness of greater than 200 microns. Larger, more rigid implants have a more significant role on the overall biomechanics of the cornea, imposing a curvature change on the anterior surface of the cornea.

Corneal implants are utilised to correct visual impairment by altering the corneal shape, specifically the curvature of the corneal surface anteriorly and posteriorly. They can be classified into 2 distinct and self-explanatory groups; onlays are implants that are placed over the anterior surface of the cornea, whereas inlays are surgically implanted into the substance of the cornea. Both onlays and inlays are designed to illicit a change in the refractive power of the cornea by altering or compensating the curvature of the refractive surfaces.

Other methods of refractive error correction include LASIK, a procedure that employs a laser to remodel a portion of the cornea. The laser is focused onto a central area of the cornea guided by topographical imaging after a corneal flap is lifted. However, this widely used procedure however offers no further ability to re-correct refractive error when vision regresses if the cornea is too thin to allow further LASIK procedures.

The need for improved corneal implants and methods of correcting various types of corneal refractory errors remains.

SUMMARY

One aspect of the invention is a method of corneal refractive error correction. One part is a series of corneal arches both placed horizontally and along the radius of curvature of the cornea to be inserted into the cornea within a specific pattern. The aim is to manipulate the irregular anterior and posterior corneal surface to correct refractive error and presbyopia. The correct combination of corneal arches shall be determined by a guidance programme that will calculate the needed length, width and radius of curvature of each arch. Moreover, the guidance programme will also provide the accurate radial and circumferential position and depth of each arch implant. Implantation of the implant shall be made into a femtosecond laser assisted incision/ pocket within the corneal stroma or by manual creation of the pocket by the surgeon using a special instrument or knife. By following the implantation instructions created by the guidance programme the implants are inserted in consecutive fashion and induce the desired corneal shape.

In some embodiments, the present disclosure provides an intra corneal implant comprising a peripheral base end portion, a central tip portion, and an arched portion including two generally opposed edges connecting the peripheral base end portion and the central tip portion.

In other embodiments, the present disclosure provides an implant comprising a circumferential substantially planar shape, an inner arched edge, and outer arched edge, a smooth inferior face and a notched superior face, wherein the notched superior face includes a plurality of notches sized and shaped to mate with the two generally opposed edges of an inter corneal implant as described herein.

In other embodiments, the present disclosure provides a method of treating an eye of a subject, the method comprising forming an incision in a cornea of the eye of the subject, and inserting an intra corneal implant into the incision.

DETAILED DESCRIPTION

Figure 1:
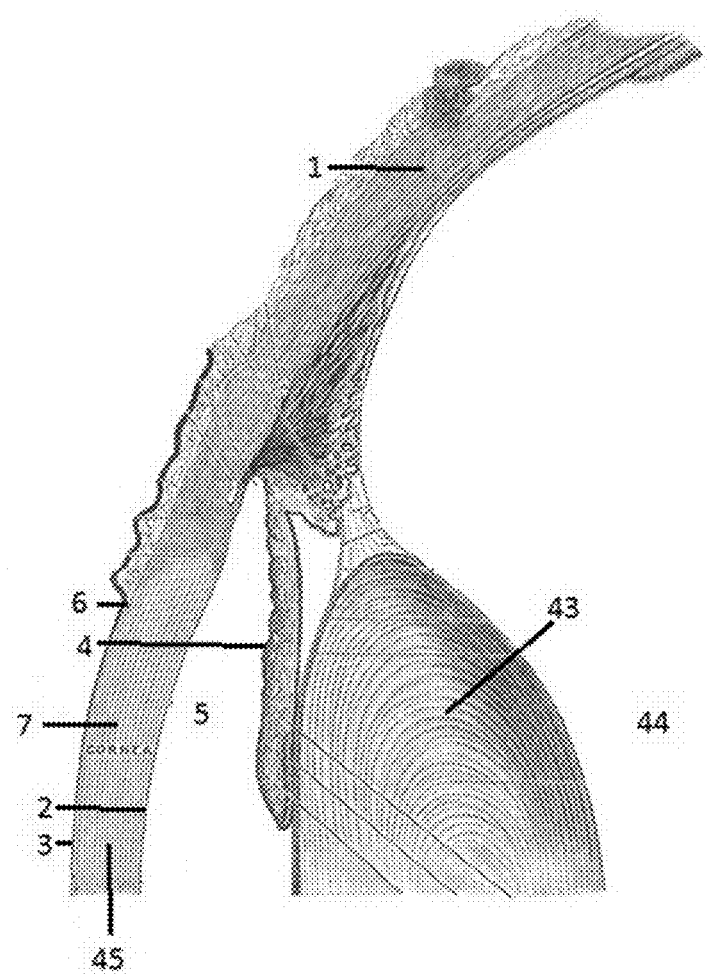
FIG. 1 is an anatomical sketch of the anterior chamber of the eye, including corneal structures.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

References to "one embodiment," "an embodiment," "example embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

As used herein the term "method" refers to manners, means, techniques and procedures for accomplishing a given task including, but not limited to, those manners, means, techniques and procedures either known to, or readily developed from known manners, means, techniques and procedures by practitioners of the surgical, pharmacological, biological, biochemical and medical arts.

Referring to FIG. 1 of the drawings is a horizontal cross section of the anterior chamber of the human eye. The lens 43 is a transparent bi-convex body of crystalline protein that is placed between the vitreous 44 and the iris 4. The diameter of the lens varies markedly and is dependent upon the accommodative mechanism of the eye. The cornea 7 is the outermost fibrous, collagenous transparent coating of the front of the eye. Its curvature is greater than the rest of the human eye and is ideally spherical in nature. The central portion of the cornea is called the optical zone 8 and the surrounding area gradually flattens as the cornea thickens going peripherally. In further detail the cornea is seen to be made up of layers with the outermost being the epithelium 3. Here cells on the surface function to maintain transparency of the cornea and to provide nutrition to the stroma 45, otherwise known as the substansia propria. The stroma 45 is comprised of a lamella or layers having bands of fibrous collagen running parallel to each other. The pattern of fibres run in different directions in each layer. It is here that the implants whether circumferential, radial or both are inserted and it is within this stroma that the stromal patterns are cut. The endothelial layer 2 is the most posterior layer of the cornea and is made up of a single layer of cells. The limbus 6 is the transition zone between the cornea 7 and the sclera 1.

Figure 2:
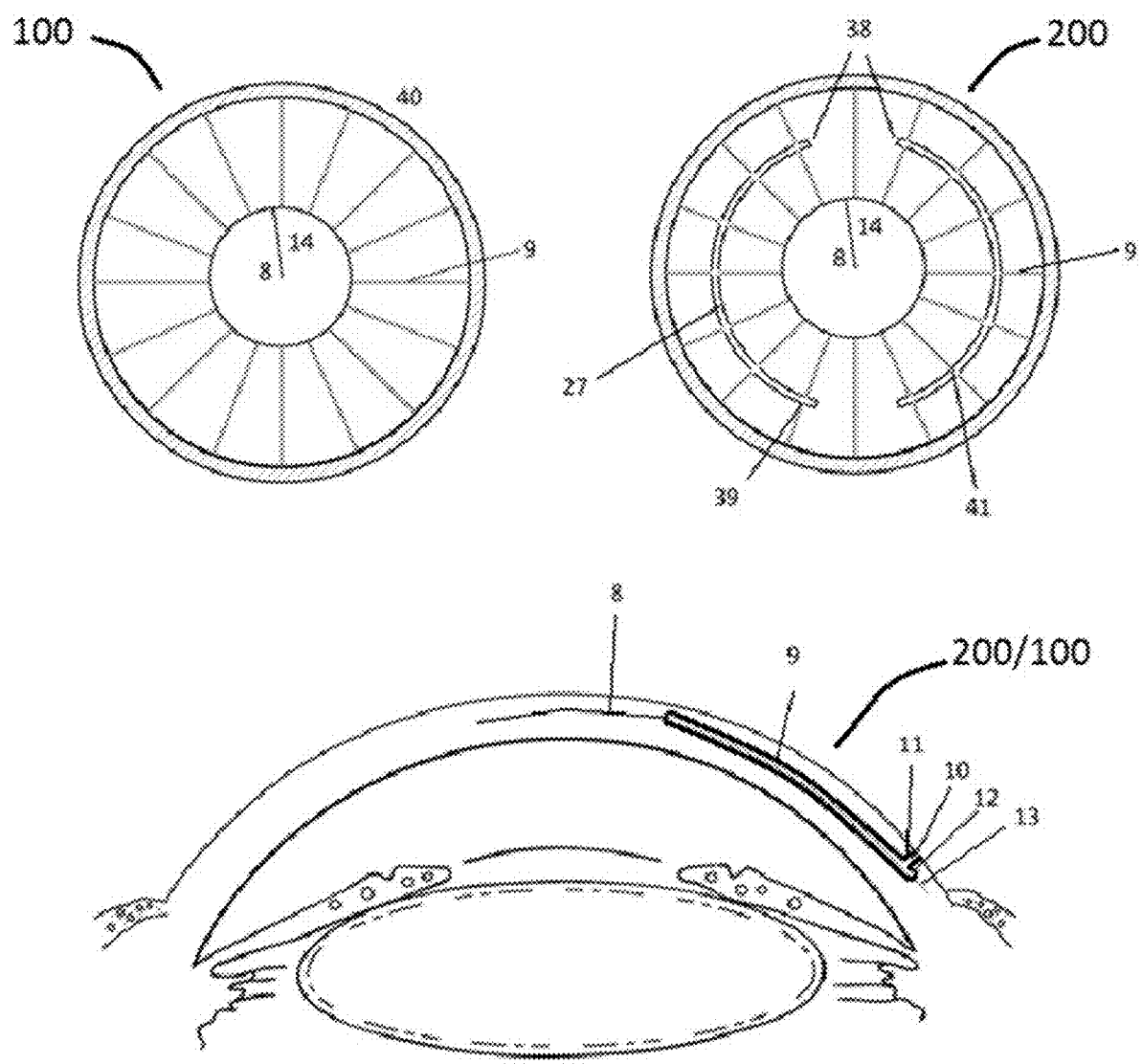
FIG. 2 shows the maximal corneal incision pattern showing a plurality of radial pocket incisions and circumferential incisions in the corneal stroma according to one embodiment of the present disclosure.

Shown in FIG. 2 is one embodiment of a pattern of corneal incisions that may be created (e.g., using a femtosecond laser) using a guidance programme for accurate incision location. The upper images demonstrate how radial only incisions (upper left) and radial and circumferential incisions (upper right) may be incised. In some embodiments, the incision pattern is unequal and/or uneven in distribution in order to correct certain refractive errors. In other embodiments, such as those shown in FIG. 2, the incisions are distributed substantially equally and evenly. In the embodiments shown in FIG. 2, the individual radial spokes of each radial pocket 9 span from the limbal area 40 via a straight line (when viewed from above) to the outer edge central optical zone 8. The apical tip of each radial arch may approach (e.g., abut), but preferably should not encroach on, the optical zone 8 which typically has a radius 14 of about 3 mm.

The upper right diagram of FIG. 2 shows radial incisions 9 in combination with two circumferential corneal incisions 47. The circumferential corneal incisions 47 include an entrance point 38 that is in communication with the anterior cornea surface. In some embodiments, the circumferential incision 47 include an angulated upturn, for example at 90 degrees, portion that is in communication with the entrance point 38 and the circumferentially-shaped portion. In some embodiments, one or two circumferential incisions 47 are created. In embodiments, a first circumferential incision 47 is created with an entrance point at an approximately 11 o'clock position (viewing the cornea as a clock face with 12 o'clock referring to the top of the eye when the patient is standing) and ending at an approximately 7 o'clock position. In other embodiments, a second circumferential incision 47 is created with an entrance point 38 at an approximately 1 o'clock position and ending at an approximately 5 o'clock position. In other embodiments, a first circumferential incision 47 is created with an entrance point at an approximately 11 o'clock position and ending at an approximately 7 o'clock position, and a second circumferential incision 47 is created with an entrance point 38 at an approximately 1 o'clock position and ending at an approximately 5 o'clock position.

In some embodiments, each circumferential corneal incision 47 is in communication with any overlapping radial incisions 9. In some such embodiments, the circumferential incisions 47 are formed in the same plane as the radial incisions 9, for example by the computer programme-assisted femtosecond laser. Accordingly, in some embodiments, the incision pattern includes one or more intersections between the limbal side of the circumferential incision 47 and the radial incision 9 (i.e., limbal incision junction 39) and one or more intersections between the central side of the circumferential incision 47 and the radial incision 9 (i.e., central incision junction 41).

Figure 3:
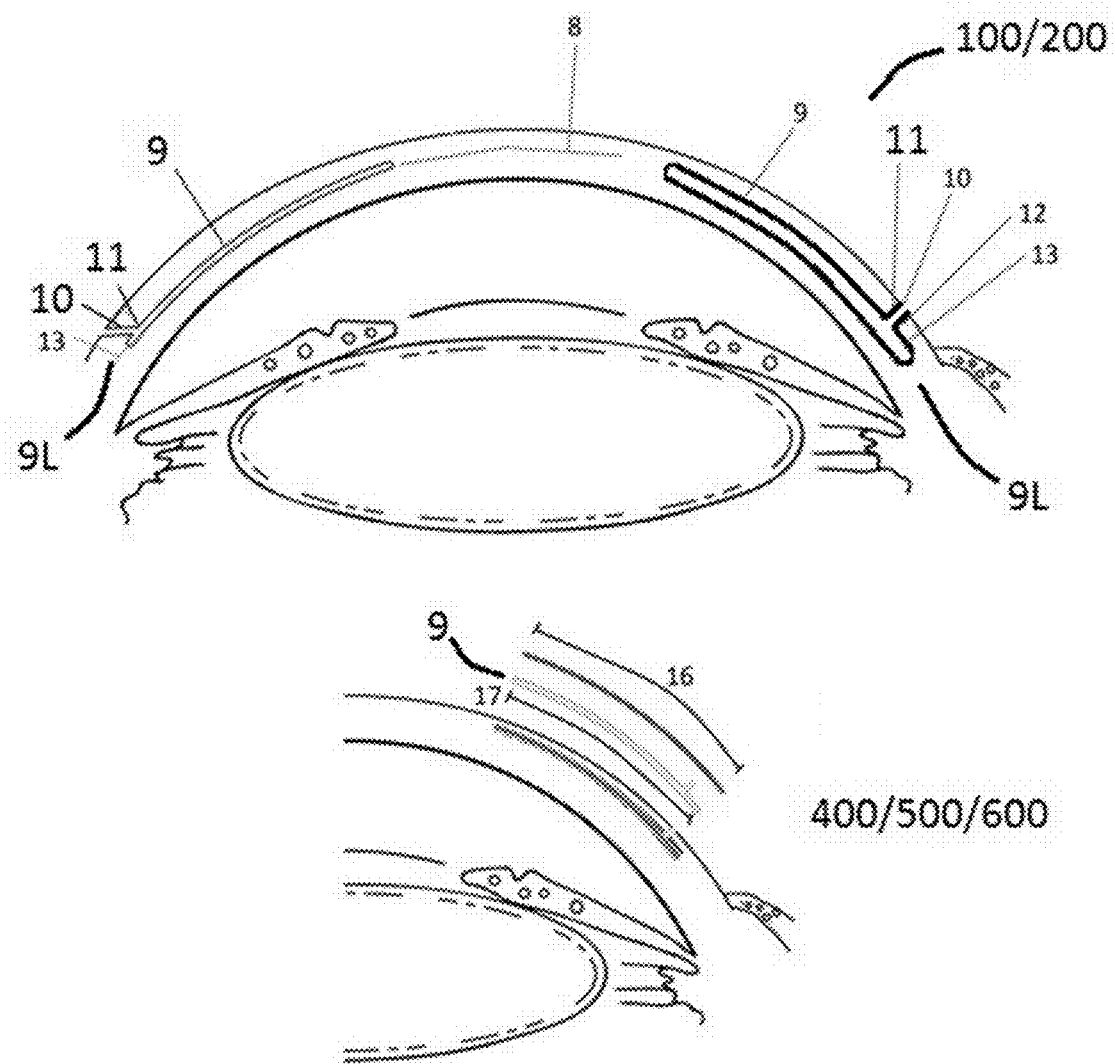
FIG. 3 is a cross-sectional schematic drawing showing a variety of depths and lengths of incisions suitable for use in connection with the present disclosure.

The lower portion of FIG. 2 depicts the radial pocket 9 in cross section, including the communicating branch 10. Embodiments including the communicating branch 10 provide a convenient entry point of the implants (e.g., radial implant 9) into the pocket. In some embodiments, the communicating branch is located toward the central optical zone 8 from the limbal end 9L (FIG. 3) of the radial incision 9. In such embodiments, the radial implant 400/500/600 is pushed back to the periphery (e.g., towards limbal end 9L), reducing or eliminating the risk that the radial implant 400/500/600 may be expelled from the cornea. In some embodiments, the communicating branch 10 may be formed at an essentially right angle to the radial incision 9. In other embodiments, the communicating branch 10 may be angled towards the limbus and away from the central optical zone 8 to allow for easier manipulation and greater stability. The distance 11 is the length of the communicating branch 10. As shown in FIG. 3, the length of the communicating branch 10 may vary at least as a function of the angle formed between the communicating branch 10 and the radial incision 9. In some embodiments, the communicating branch 10 has a length of about 100 microns to about 300 microns.

The depth of the radial incision 9 (e.g., the distance between the radial incision 9 and corneal surface) may be determined by analysis of topographical data that is associated with the cornea, for example as taken (e.g., measured) from the patient during an examination. The depth may vary from patient to patient in order to induce a required shape change within the cornea. The distance 13 is the distance between the limbal edge 9L of the radial incision 9 and the limbal edge of the cornea. In general, the radial incision 9 has a length 17 that corresponds to the distance between the limbal edge of the cornea and the limbal edge of the central optical zone 8 less the distance 13 between the limbal edge 9L of the radial incision 9 and the limbal edge of the cornea. In some embodiments, the length 17 is less than the length 17 of the radial implant 400/500/600. In some embodiments, the length 17 is about 0.05 mm to about 0.5 mm less than the length 16 of the radial implant 400/500/600, for example about 0.05 mm less, about 0.06 mm less, about 0.07 mm less, about 0.08 mm less, about 0.09 mm less, about 0.1 mm less, about 0.11 mm less, about 0.12 mm less, about 0.13 mm less, about 0.14 mm less, about 0.15 mm less, about 0.16 mm less, about 0.17 mm less, about 0.18 mm less, about 0.19 mm less, about 0.2 mm less, about 0.21 mm less, about 0.22 mm less, about 0.23 mm less, about 0.24 mm less, about 0.25 mm less, about 0.26 mm less, about 0.27 mm less, about 0.28 mm less, about 0.29 mm less, about 0.3 mm less, about 0.31 mm less, about 0.32 mm less, about 0.33 mm less, about 0.34 mm less, about 0.35 mm less, about 0.36 mm less, about 0.37 mm less, about 0.38 mm less, about 0.39 mm less, about 0.4 mm less, about 0.41 mm less, about 0.42 mm less, about 0.43 mm less, about 0.44 mm less, about 0.45 mm less, about 0.46 mm less, about 0.47 mm less, about 0.48 mm less, about 0.49 mm less, or about 0.5 mm less than the length 16 of the radial implant 400/500/600.

Figure 4:
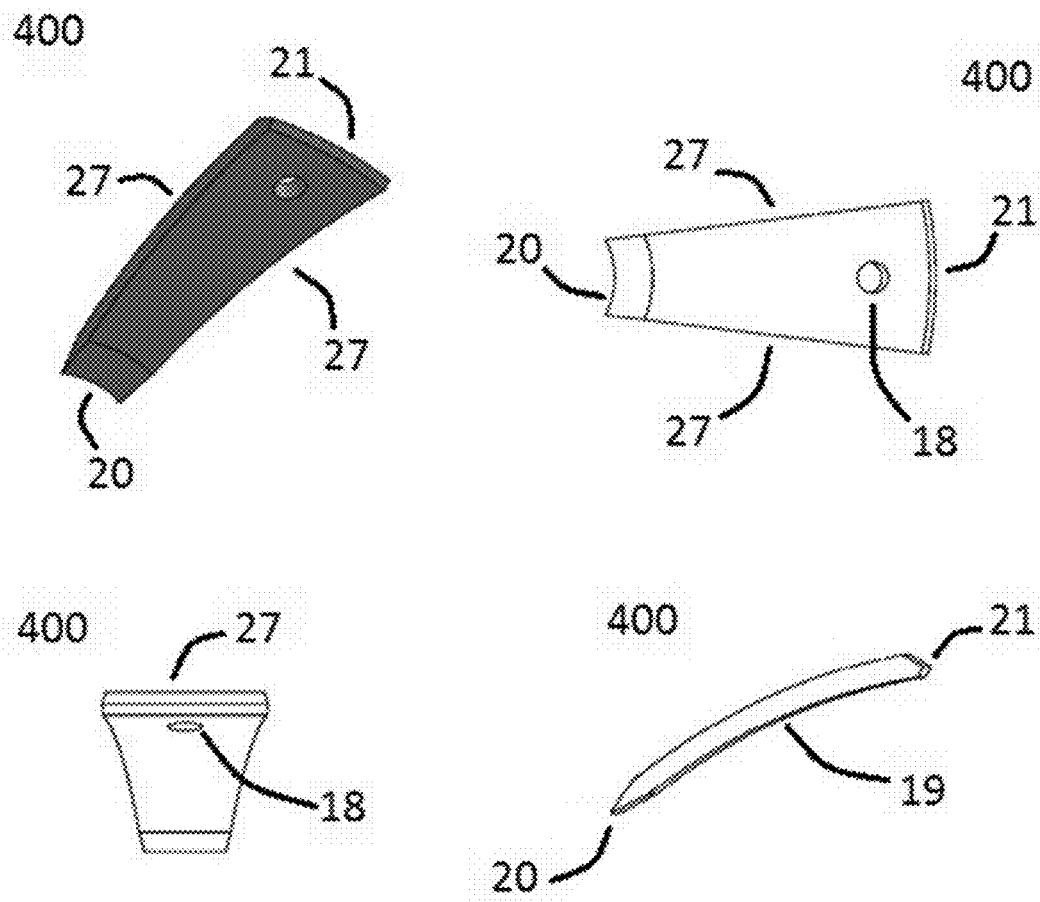
FIG. 4 is a schematic drawing showing individual basic radial corneal arches according to embodiments of the present disclosure.
Figure 5:
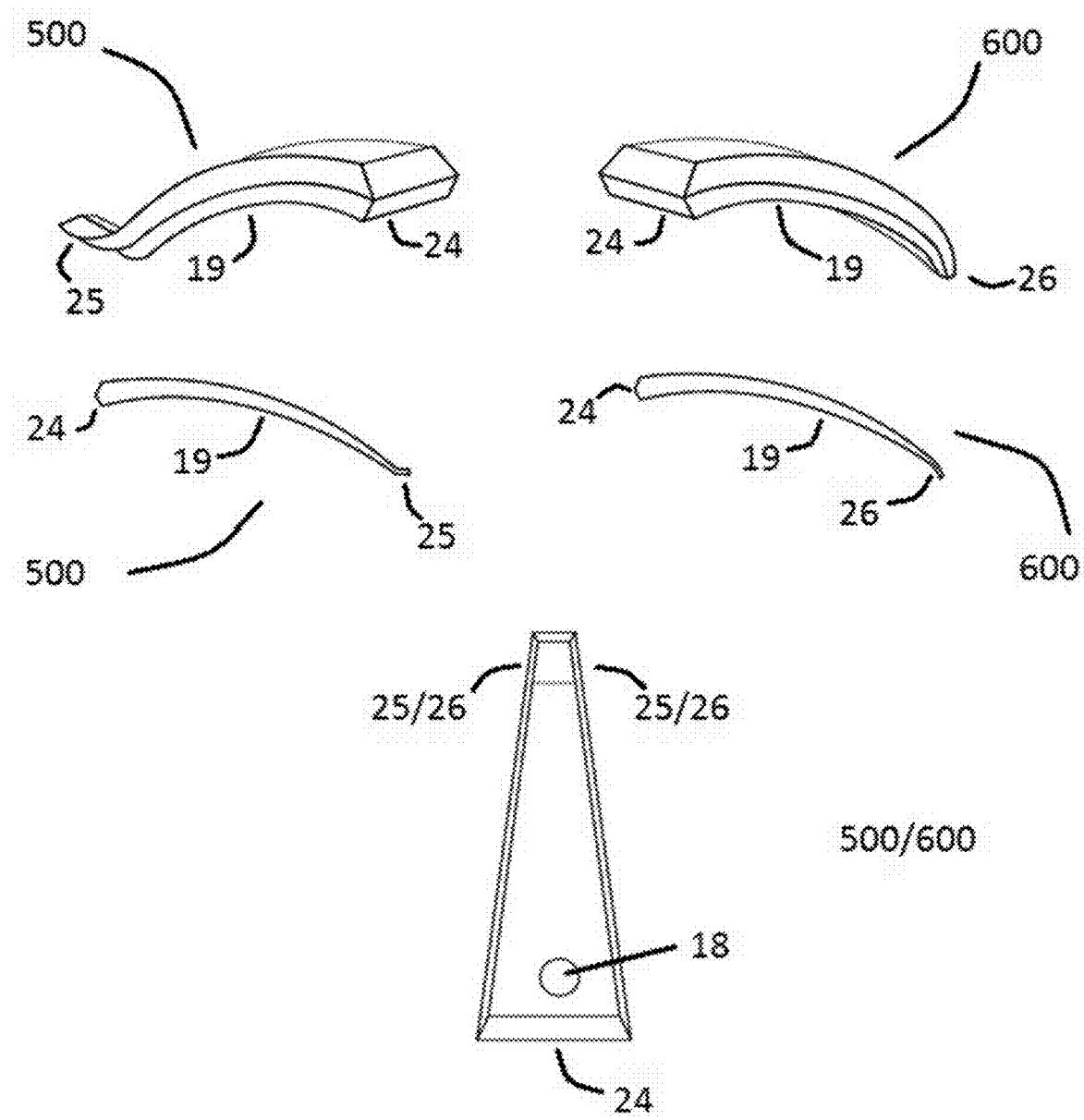
FIG. 5 is a schematic drawing showing individual presbyopic radial corneal arches suitable for use in correcting presbyopic refractory errors in an eye according to one embodiment of the present disclosure.

Referring now to FIG. 4, the present disclosure provides a radial implant 400 comprising a trapezoidal single piece construction. The radial implant 400 includes a peripheral base end 21 and a central tip portion 20, and an arched portion 19 having generally opposing edges 27 and being tapered from the peripheral base end 21 to the central tip portion 20 in both the cross sectional and sagittal view. The radius of curvature of the arched portion 19 gives the radial implant 400 a specific curvature to induce a shape change within the cornea upon implantation. The specific radius of curvature of the arched portion 19 can be different, for example as shown in radial implant 400 (FIG. 4), radial implant 500 (FIG. 5) and radial implant 600 (FIG. 5). In general, with the smaller degrees of radius of curvature (i.e., more dramatic curvature) of the arched portion 19 corresponding to more pronounced curvature to the radial implant 400/500/600.

As also shown in FIG. 4, radial implant 400 may include two straight edges 47. The edges 47 may be tapered in order to provide an implant 400 having a generally hexagonal cross section. Implantation of a radial implant 400 having tapered edges 47 into a radial incision 9 may be less prone to removal (e.g., expelled) from the cornea, for example by causing the radial corneal incision 9 to widen from the force the tapered edges 47 impart on the side walls of the radial incision 9. The central tip portion 20 may be curved inwardly (e.g., in a concave manner) to avoid obscuring a portion of the central optical zone 8. The peripheral base end 21 may be curved outwardly (e.g., in a convex manner), for example to match the curvature of the limbal area of the cornea. One example of a suitable hexagonal cross sectional shape is shown in the bottom left portion of FIG. 4; in this embodiment the cross sectional shape is widest near the peripheral base end 21 narrowest at near the central tip portion 20. In another embodiment, the implant 400 includes a rectangular or oval cross section.

In some embodiments, the radial implant 400 additionally includes a manipulation hole 18. In some embodiments, the manipulation hole 18 is a superior to inferior hole near the peripheral base end 21. The manipulation hole 18 is sized to reversibly mate with a manipulation tool for enabling a clinician to adjust the placement of the radial implant 400 during implantation and is generally positioned midway between generally opposing sides 27. In some embodiments, the manipulation hole 18 is up to about 0.5 mm in diameter.

Figure 6:
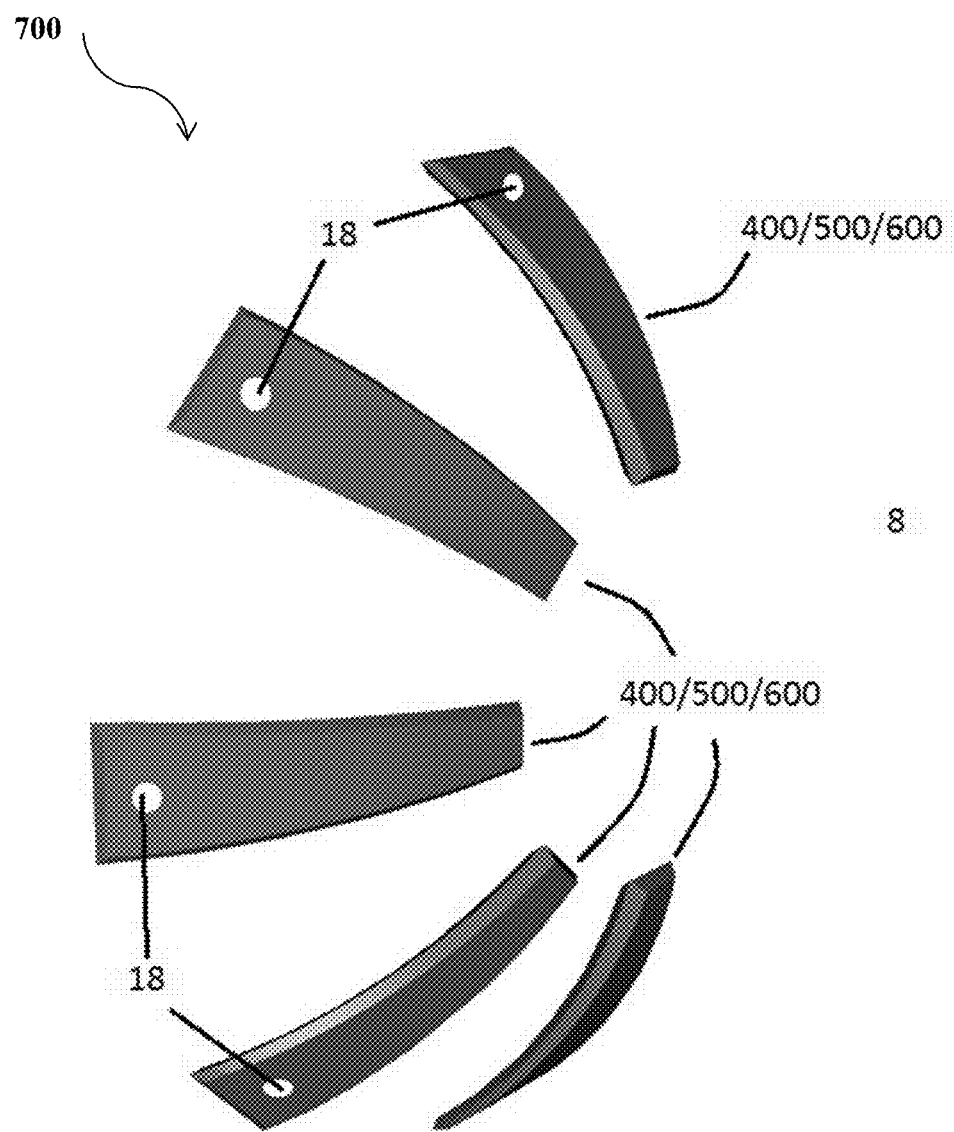
FIG. 6 shows a configuration of radial corneal arches according to one embodiment of the present disclosure.

Referring now to FIG. 5, another embodiment of a radial implant 500 includes a similar overall shape to radial implant 400 of FIG. 4, however the central tip portion 25 of radial implant 500 includes an upward inflection (e.g., towards the surface of the cornea. Once implanted into the cornea, the upwardly inflected central tip portion 25 may induce flattening of the central part of the cornea, for example in cases of myopia where the central cornea is too steeply curved. When a plurality of radial implants 500 of this embodiment are implanted about the central part of a cornea (for example as shown representatively in FIGS. 6-8), the net circumferentially applied outward force will pull parts of the cornea toward the limbal edge in every direction resulting in an overall flattening effect. The degree to which the central cornea must be flattened and consequently the angle of upward inflection of the radial implant 500 may be determined by a guidance programme.

Also shown in FIG. 5 is another embodiment of a radial implant 600 with similar features as radial implant 400 and radial implant 500, except radial implant 600 includes a central tip portion 26 that includes a downward inflection (e.g., away from the surface of the cornea). Radial implants 600 consistent with this embodiment may induce a steepening of the central cornea when needed, for example in cases of hyperopia, where the central cornea is too flat. When a plurality of radial implants 600 of this embodiment are implanted about the central part of a cornea (for example as shown representatively in FIGS. 6-8), the net circumferentially applied inward force will pull parts of the cornea toward the central optical zone 8 resulting in a net overall steepening effect. The degree to which the central cornea must be steepened and consequently the angle of downward inflection of the radial implant 600 may be determined by a guidance programme The radial implant(s) 400/500/600 may be introduced into the individual radial incision(s) 9 after the appropriate incision pattern has been made in the cornea, for example using a femtosecond laser. In some embodiments, the radial implant(s) 400/500/600 is grasped and manipulated at the peripheral base end 20/25/26 by standard surgical microforceps with angulation of the forceps tip preferable, once the surgeon is comfortable with the manipulation and grasp of the radial arch the tip is introduced to the opening that leads into the communication branch 10, with gradually progressing down the branch and into the radial incision 9. The surgeon then manipulates the eye such that the plane that the radial corneal pocket resides in is the same as the plane of the radial implant(s) 400/500/600; once this is achieved the radial implant(s) 400/500/600 may be further introduced into the radial incision 9. The radial implant(s) 400/500/600 has a length 16 which is slightly longer than the of the radial incision length 17 so that the when fully introduced the radial implant(s) 400/500/600 fits securely within the radial incision 9. The tight fit is achieved when the radial implant(s) 400/500/600 is introduced gradually against resistance into the radial incision 9; when the radial implant(s) 400/500/600 reaches the end of the radial incision 9 nearest the central optical zone 8, the force exerted on the radial implant(s) 400/500/600 and consequently on the edges of the radial incision 9 tend to expand the edges of the radial incision 9. Once the edge of the radial incision 9 is reached and expanded by the central tip portion 20/25/26 and side edges 47, the surgeon may remove the forceps and use a manipulator tool (e.g., a tool with a curved or right angled tip) via the manipulation hole 18. The surgeon may then further introduce the radial implant(s) 400/500/600 into the radial incision 9 in such a manner that the peripheral base portion 21/24 of the radial implant(s) 400/500/600 along with the tip of the manipulator tool is fully introduced into the radial pocket. Once the radial implant(s) 400/500/600 has bypassed the end of the communicating branch 10, the manipulating tool may be disengaged from the manipulation hole 18 and the radial implant(s) 400/500/600 may be moved within the radial incision 9 so that the peripheral base portion 21/24 is near or against the limbar end 9L of the radial incision 9.

Figure 7:
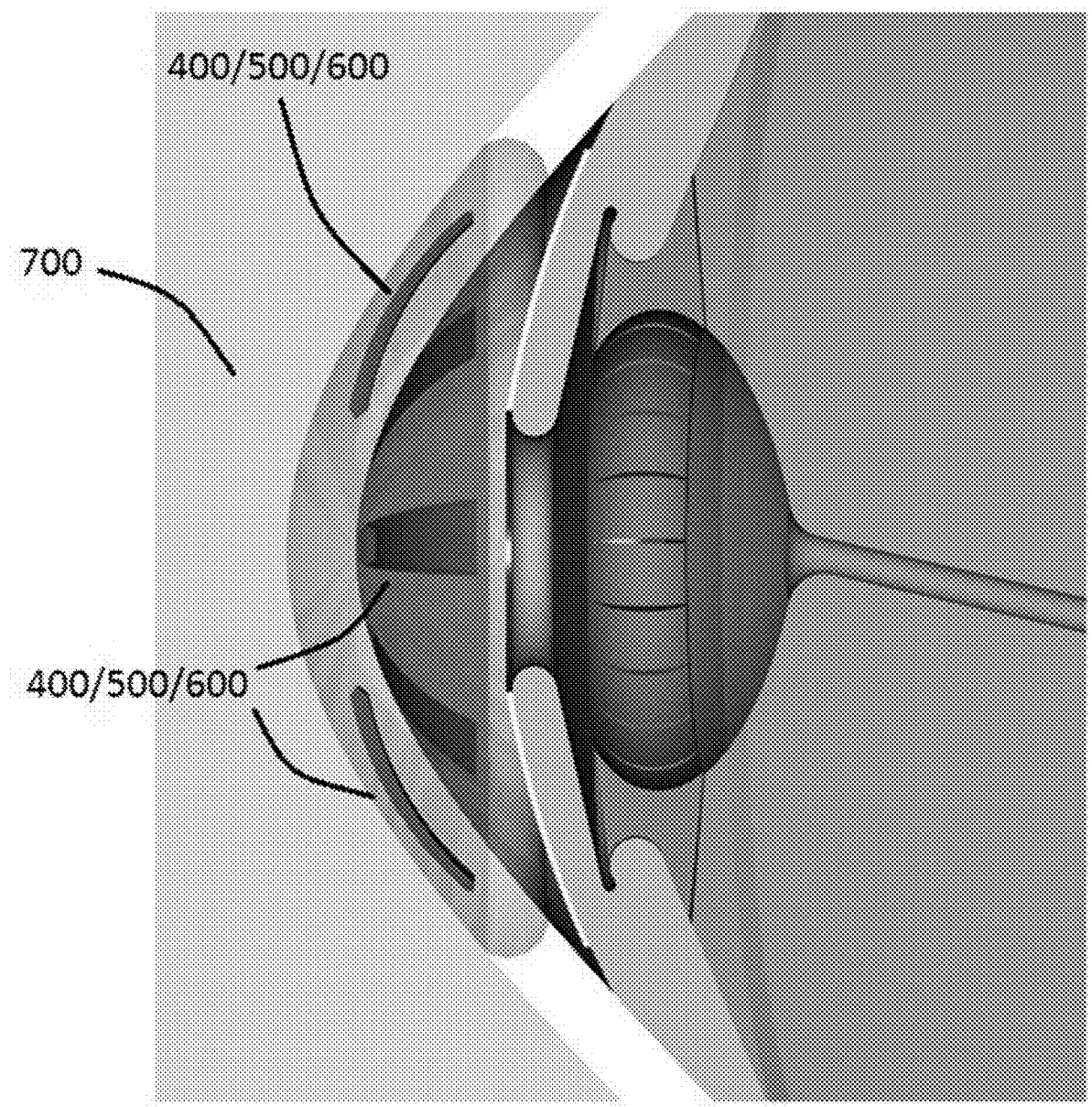
FIG. 7 is a cross-sectional view of a cornea with radial corneal arches in situ according to one embodiment of the present disclosure.
Figure 8:
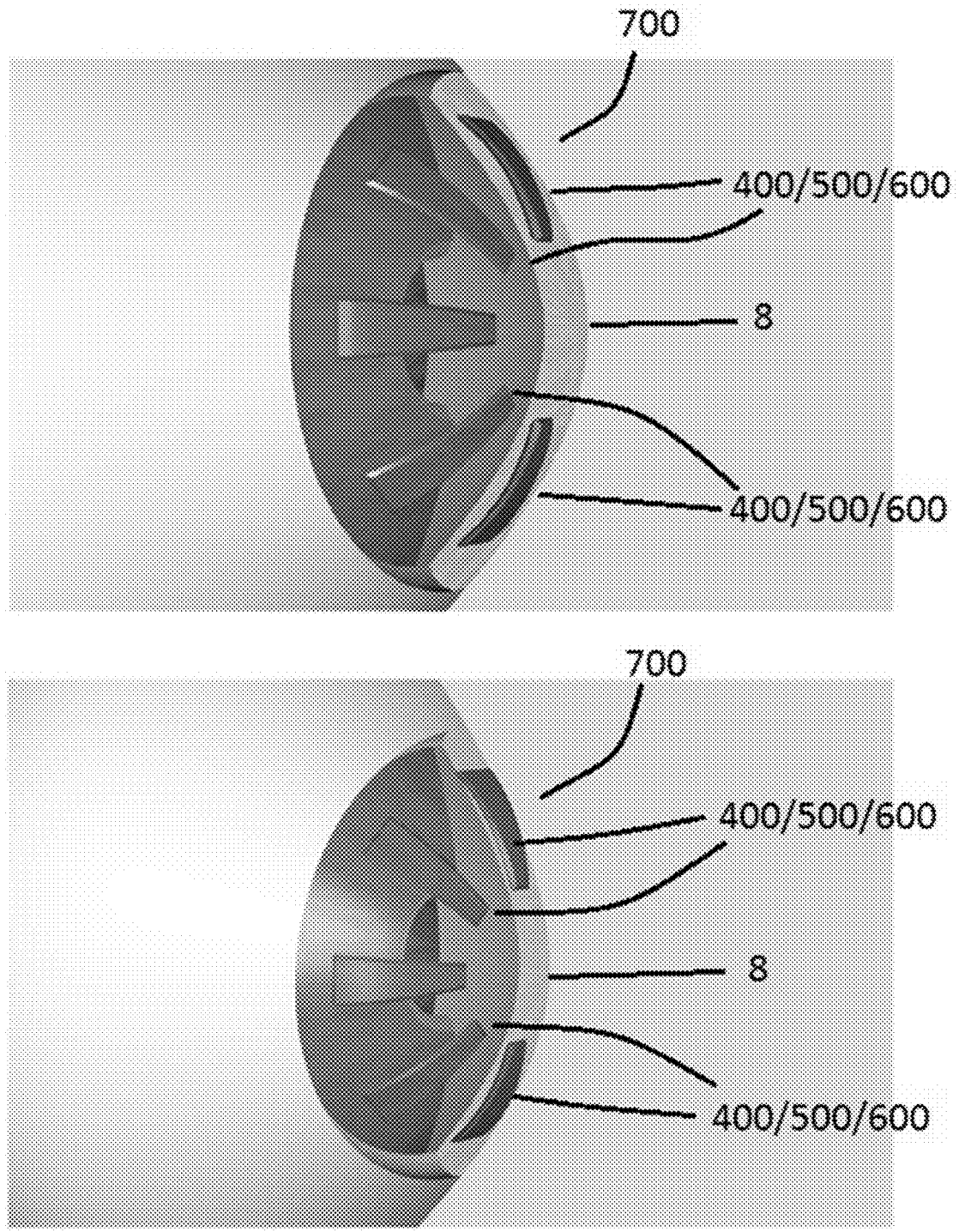
FIG. 8 is a cross-sectional view of a cornea with a combination of radial arches in situ according to one embodiment of the present disclosure.
Figure 9:
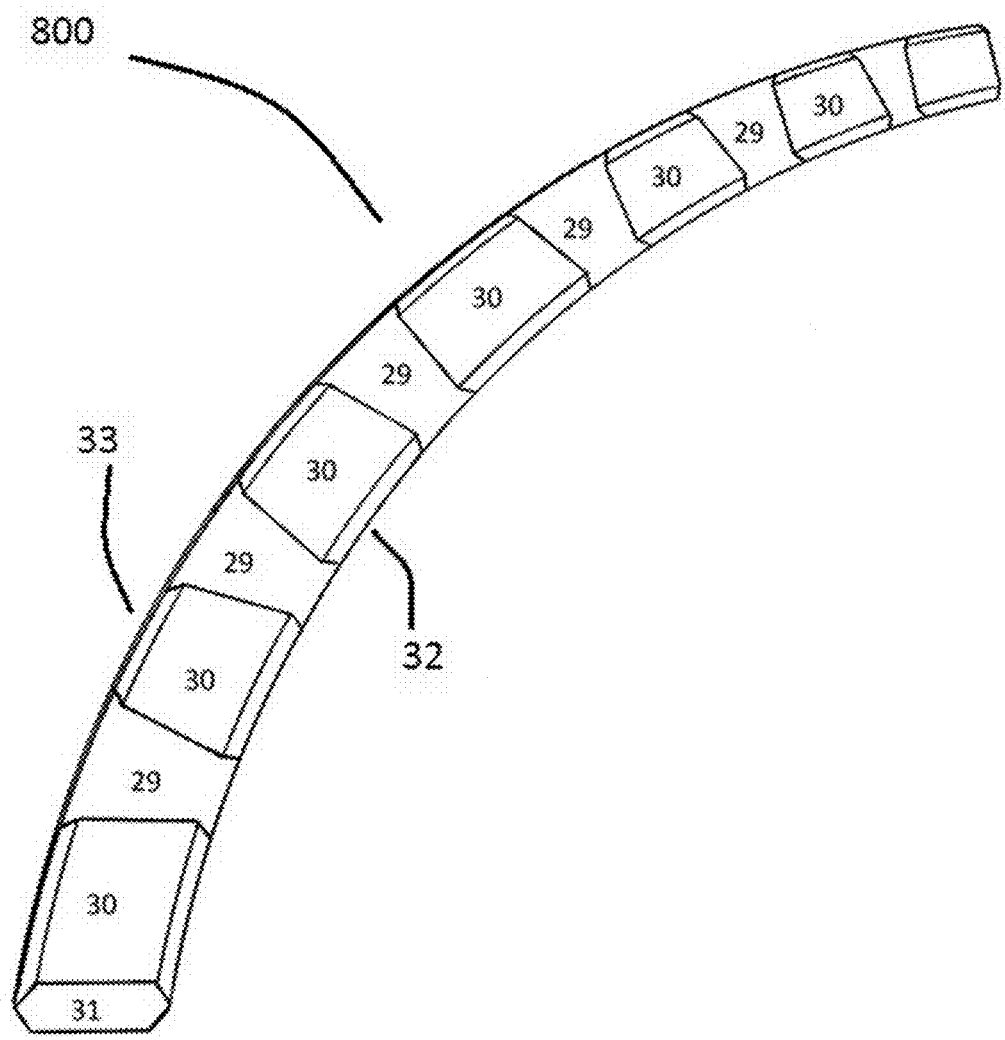
FIG. 9 shows a circumferential corneal arch implant according to one embodiment of the present disclosure.
Figure 10:
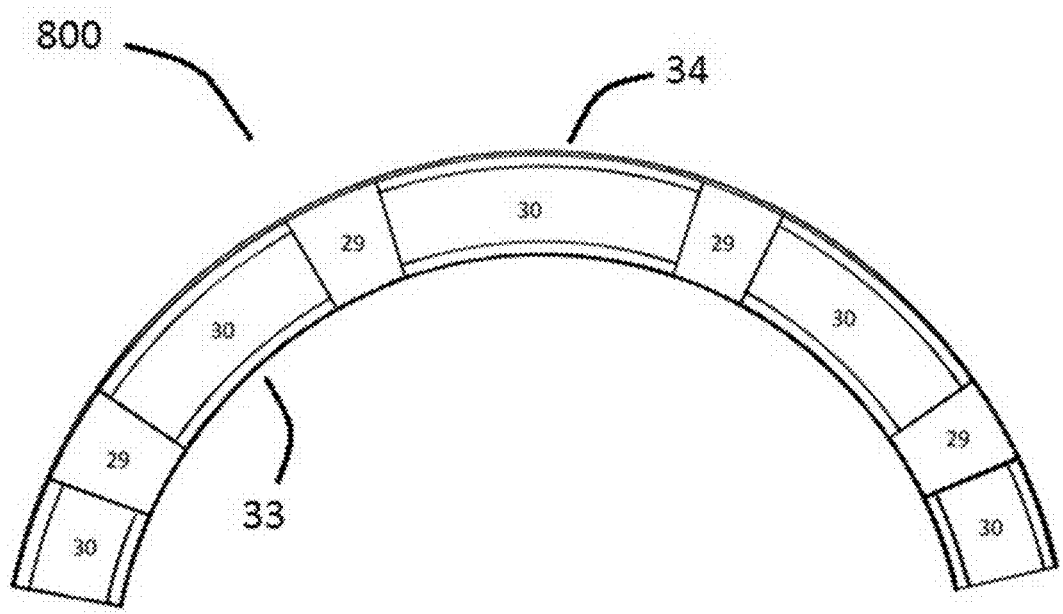
FIG. 10 shows a circumferential corneal arch implant according to one embodiment of the present disclosure.

FIGS. 7, 8 and 9 demonstrate the shape of the radial implants 400/500/600 after implantation into the corneal stroma. Illustrated is the clear central optical zone 8 of the cornea that is not encroached upon by the central tip portions 20/25/26.

Referring now generally to FIGS. 4 and 9-12, a circumferential corneal implant 800 may be implanted about the central optical zone 8 of the cornea prior to inserting the radial implant(s) 400/500/600. The circumferential implant 800 may include notch spaces 29 on the superior surface 36, with inter-notch areas 30 between each notch 29. The location of the notch spaces 29 may correspond to desired spacing of radial implants 400/500/600, for example as determined by a guidance programme based at least in part on topographical information associated with the cornea. Thus, the notch spaces 29 are sized and shaped to mate with radial implants 400/500/600 (see FIG. 12) in order to form an interlocked network of implants inside the radial incisions 9 and the circumferential incision 47. Such an interlocked network of implants may be useful, for example, when a substantial change in corneal curvature is required.

In some embodiments, the notch spaces 29 are generally wedge-shaped, with a wider opening at the limbal side 33 and a narrower opening at the central side 32. Such a configuration will limit the progression of the radial implant 400/500/600 as it is slid into the radial incision 9 and through the notch 29.

Figure 11:
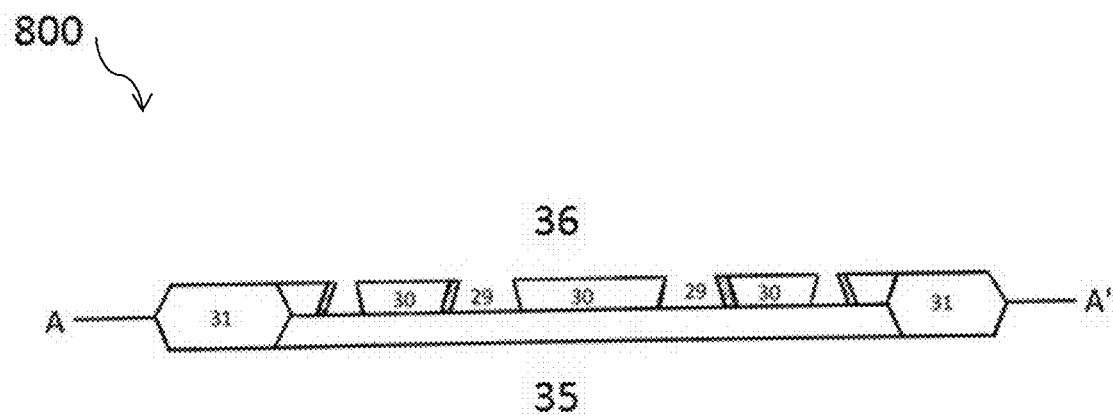
FIG. 11 shows a circumferential corneal arch implant according to one embodiment of the present disclosure.
Figure 12:
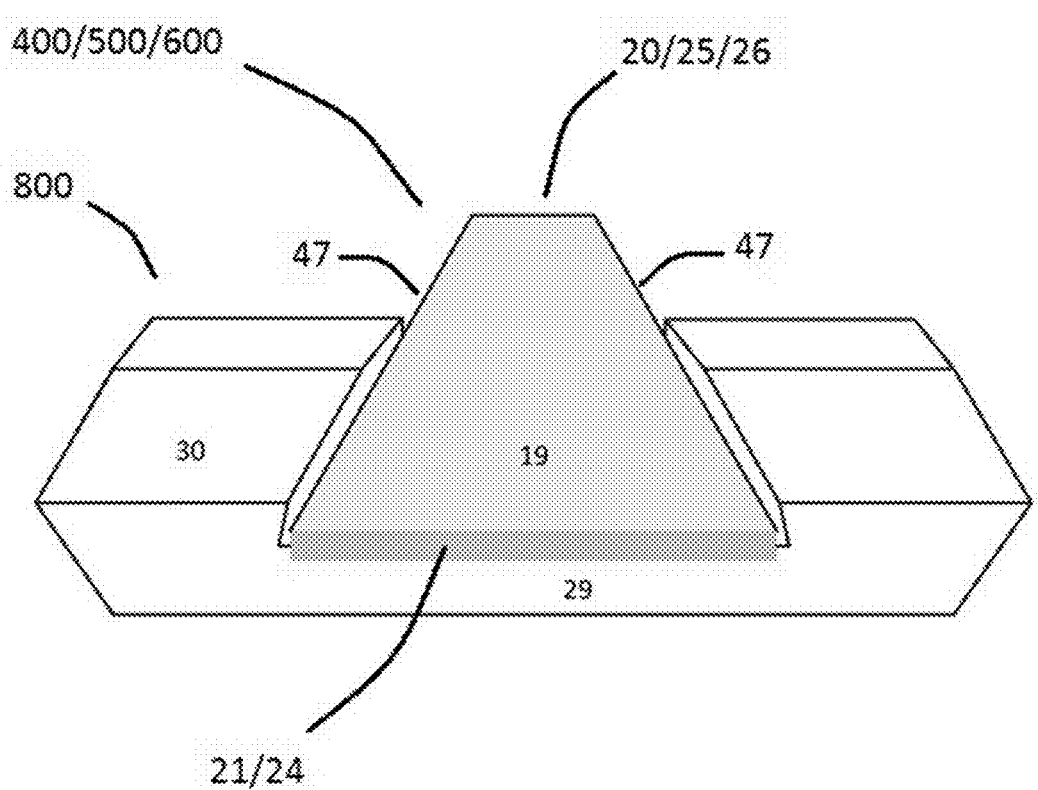
FIG. 12 shows a radial corneal arch implant inserted into inter-notch spaces of a circumferential corneal arch implant according to one embodiment of the present disclosure.

The circumferential implant 800 may have a cross section 31 that is generally hexagonal in shape, with varying radius of curvature. FIG. 11 shows the arch in horizontal view with its inferior face 35 and superior 36 face. In some embodiments, the A-A' plane matches the plane of curvature of the cornea upon implantation.

In some embodiments, a circumferential incision 47 is made in the cornea before implanting the circumferential corneal implant 800. In some embodiments, the size, shape and location circumferential incision 47 are determined based at least in part on topographical information associated with the cornea, and the circumferential incision may be made in the cornea using a computer-controlled laser such as a femtosecond laser. In some embodiments, the circumferential incision 47 is cut while the radial incision(s) 9 are cut.

In some embodiments, the circumferential incision 47 is in communication with the radial incision(s) 9. For example, as shown in FIG. 4, the circumferential incision 47 is connected to the radial incision 9 at point 39 where the two pockets are at the same plane. The circumferential incision 47 is open to the anterior surface of the cornea at point 38 where the circumferential incision 47 gradually deviates to the surface of the cornea. The circumferential corneal implant 800 may be inserted into the circumferential incision 47 using standard micro surgical forceps. The circumferential implant 800 is inserted with the notched face 36 towards the anterior cornea surface and with the central side 32 towards the central optical zone 8.

Accordingly, in one embodiment the present disclosure provides an intra corneal implant comprising a peripheral base end portion, a central tip portion, and an arched portion including two generally opposed edges connecting the peripheral base end portion and the central tip portion. In some embodiments, the peripheral base end portion is wider than the central tip portion. In some embodiments, the peripheral base end portion is curved. In some embodiments, the peripheral base end portion is curved outwardly. In some embodiments, the central tip portion comprises a curved edge. In some embodiments, the curved edge is curved inwardly. In some embodiments, the intracorneal implant has a generally hexagonal cross sectional shape. In some embodiments, the central tip portion has a tapered cross sectional shape. In some embodiments, the peripheral base portion has a tapered cross sectional shape. In some embodiments, the intra corneal implant further comprises a manipulation hole through the arched portion. In some embodiments, the central tip portion includes an upward inflection. In some embodiments, the central tip portion includes a downward inflection. In some embodiments, the intra corneal implant has a refractive index similar to that of a cornea. In some embodiments, the intra corneal implant is made of a bioinert, rigid material. In some embodiments, the intra corneal implant comprises a polymer, for example a poly methyl methacrylate (PMMA), a hydrophobic acyrlics or a hydrophylic acrylics with low degrees of hydration. In some embodiments, the intra corneal implant comprises a synthetic collagen, or a collagen material. In some embodiments, the intra corneal implant includes a color tint. In some embodiments, the arched portion has a radius of curvature of about 6 mm to about 10 mm. In some embodiments, the intra corneal implant has a length of about 3 mm to about 5 mm, a width of about 0.5 mm to about 1.5 mm, and a cross sectional thickness of about 50 microns to about 200 microns. In some embodiments, the two generally opposed edges are tapered.

In other embodiments, the present disclosure provides an implant comprising a circumferential substantially planar shape, an inner arched edge, and outer arched edge, a smooth inferior face and a notched superior face, wherein the notched superior face includes a plurality of notches sized and shaped to mate with the two generally opposed edges of the inter corneal implant as described herein. In some embodiments, the plurality of notches include tapered edges for mating with two tapered generally opposed edges of an inter corneal implant as described herein.

In some embodiments, the radial implant 400/500/600 and/or the circumferential implant 800 is formed of a clear biocompatible material, such as PMMA plastic. In some embodiments, the radial implant 400/500/600 and/or the circumferential implant 800 is clear (e.g., colorless and transparent). In other embodiments, the radial implant 400/500/600 and/or the circumferential implant 800 may include a color tint.

Therapeutic Methods

In some embodiments, a patient with a refractive error is scanned and topographical data (e.g., current corneal curvature and corneal thickness) corresponding to one or more of the patient's corneas is determined. Refractive errors to be corrected may include hyperopia, myopia, astigmatism and keratoconus in addition to presbyopia.

A finite element analysis (FEA) model corresponding to the topographical data may be generated in order to determine fixed dimensions of different combinations of the corneal implants 400/500/600 and/or circumferential implants 800 to correct the refractive error. For example, the FEA model may provide a combination, sizes, positions and incision pattern in which to insert the radial implants 400/500/600 into the patient's cornea.

In some embodiments, the FEA model provides an incision pattern. The incision pattern may then be used to create radial incisions 9 and optionally circumferential incision(s) 47 in the cornea to be treated. In some embodiments, the incisions are created by a laser, such as a femtosecond laser.

The FEA model may also provide a list or instructions (e.g., manufacturing or fabrication instructions) for a combination of radial implants 400/500/600 and optional circumferential implant(s) 800 to be implanted in the patient's cornea. The instructions may be used to fabricate (e.g., manufacture) the implants with dimensions (e.g., length 17 and curvature radius 19).

Using basic ophthalmic surgical forceps the circumferential implant 800 is typically inserted first (if it is needed to be implanted with the radial implants 400/500/600), for example using forceps, through the open end 38 of the circumferential incision 47. The radial implants 400/500/600 are then inserted through the communicating branch 10 into the radial incisions 9, for example as indicated by the instructions provided by the FEA model. If necessary, the eye is rotated or manipulated such that the radial implant 400/500/600 is within the same plane as the curvature of the cornea. Such a manoeuvre allows for easier and less traumatic insertion of the radial implant 400/500/600 into the radial incision 9. The radial implant 400/500/600 may then be gradually introduced into the radial incision 9 until the central tip portion 20/25/26 reaches the central end of the radial incision 9. During this part of the method, the central tip portion 20/25/26 encounters the notched recess 29 of the circumferential implant 800. The radial implant 400/500/600 gradually passes through the notched recess 29 until the lateral sides 27 of the radial implant 400/500/600 are in contact with the inner edges of the notched recess 29.

The peripheral edge portion 21/24 of the radial implant 400/500/600 may then be implanted using a tool with a manipulator that engages the manipulation hole 18. The tool is the used to insert the peripheral edge portion 21/24 into the limbal end 9L of the radial incision 9. The manipulating tool may then be removed from the manipulation hole 18. In some embodiments, the communicating branch 10 is left open at the end of the implantation procedure.

Accordingly, in some embodiments the present disclosure provides a method of treating an eye of a subject, the method comprising forming an incision in a cornea of the eye of the subject, and inserting an intra corneal implant into the incision.

In one embodiment, the invention comprises constructing a database of treated subjects by recording, for a plurality of subjects, a baseline corneal radius of curvature, a baseline corneal thickness, a size of intra corneal implant inserted into the eye, the incision pattern used and final corneal radius of curvature (post-surgery). In one embodiment, a desired final corneal radius of curvature in an eye can be achieved by measuring a baseline corneal radius of curvature and thickness in the eye, consulting the database for the same or similar baseline corneal radii of curvature and eye thicknesses, and selecting an implant size and/or pattern to achieve the desired final corneal radius of curvature based on implant size and/or patterns that achieved a same or similar final corneal radius of curvature in the database.

In one embodiment, the implant dimensions, number of implants, implant pattern and/or locations of incisions can be determined as a function of corneal curvature and/or thickness in the patient or in other patients.

In one embodiment, the subject has (1) a corneal thickness of no less than about 350 microns at the 7-8 mm zone of the cornea and/or (2) the patient does not have severe high degrees of keratoconus (i.e. over 58 dioptres). In one embodiment, the patient is identified or excluded as a candidate for treatment based on (1) and (2).

In some embodiments, the method further comprises forming a circumferential incision in the cornea and inserting an implant comprising a circumferential substantially planar shape into the circumferential incision. In some embodiments, the circumferential incision is in communication with an anterior surface of the cornea at an entrance point. In some embodiments, the intra corneal implant is an intra corneal implant as described herein. In some embodiments, the incision includes a radial pocket portion and a communicating branch portion in communication with the radial pocket portion and an anterior surface of the cornea. In some embodiments, the communicating branch portion forms an approximate right angle with the radial pocket portion. In some embodiments, the communicating branch portion forms an approximate right angle with the anterior surface of the cornea. In some embodiments, a length of the intra corneal implant is greater than a length of the radial pocket portion. In some embodiments, the method further comprises expanding the radial pocket portion by inserting the intra corneal implant into the radial pocket portion. In some embodiments, the step of inserting an intra corneal implant into the incision comprises inserting the intra corneal implant into the incision using forceps, and positioning the intra corneal implant using a manipulator. In some embodiments, the intra corneal implant comprises a manipulation hole and the step of positioning the intra corneal implant comprises inserting the manipulator into the manipulation hole. In some embodiments, the incision and the circumferential incision, if present, do not extend over an optical zone of the cornea. In some embodiments, the incision and/or the circumferential incision is determined based on topographical data associated with the cornea. In some embodiments, the incision and/or the circumferential incision is formed in the cornea by a laser controlled by a computer storing instructions for determining a location and dimensions of an incision and/or a circumferential incision in a cornea as a function of the topographical data. In some embodiments, the laser is a femtosecond laser. In some embodiments, the eye is a hyperopic eye, a myopic eye, an astigmatic eye, a keratoconic eye, a presbyopic eye.

EXAMPLES

Example 1

An intra corneal implant comprising an arch shaped implant to be inserted radially into the corneal stroma. Said corneal implant's use is to illicit shape and curvature change to the anterior and posterior surface of the cornea.

Example 2

An intra corneal implant comprising an arch shaped implant to be inserted circumferentially into the corneal stroma. Said corneal implant is to be used with the intracorneal implant of Example one to illicit change in the shape and curvature of the anterior and posterior surface of the cornea.

Example 3

An arch of Example 1 having a wider base section placed in the peripheral section of the cornea and a narrower tip section placed at the circumference of zone in the central cornea up to 6 mm in diameter.

Example 4

An arch of Example 1 having a hexagonal cross section throughout however the sagittal cross section is tapered in shape from the base to the tip.

Example 5

An arch of Example 1 having a circular central and peripheral edge.

Example 6

An arch of Example 1 having a refractive index similar to the refractive index of the cornea and being made of an inert polymer such as PMMA.

Example 7

An arch of Example 1, being inserted via surgical introduction and manipulation into a pre-cut radial pocket of predetermined pattern.

Example 8

An arch of Example 1 having straight edges on all 4 edges or on the radial edges.

Example 9

An arch of Example 1 having a radius of curvature ranging from 6-10 mm.

Example 10

An arch of Example 1 having a length between 3 to 5 mm and having a width ranging between 0.5 and 2.5 mm. In addition to having a cross sectional thickness ranging from 50 to 300 microns taking into account the tapered nature of the arch from base to tip.

Example 11

An arch of Example 1 having a manipulation hole of diameter 0.5 mm for intra-surgical manoeuvring.

Example 12

An arch of Example 1 being inserted into the stroma of the cornea either as a single implant or as a series of implants numbering no more than 16 arches per cornea.

Example 13

An arch of Example 1 of a specific dimension shall be placed in a pre cut corneal stromal incision in a pattern customised and predetermined according to the specific refractive error correction need of that patient and determined by the guidance programme.

Example 14

An arch of Example 1 made from coloured PMMA to illicit change of perception of eye colour.

Example 15

An arch of Example 1, in which the shape of the arch possesses an outward and upward inflection of the tip to create outward tension to flatten the central corneal section.

Example 16

An arch of Example 1, in which the shape of the arch possesses an inward and downward inflection at the tip to direct tension in the central cornea in a ring like fashion to create an increase in the central corneal curvature.

Example 17

An arch of Example 1, can additionally be inserted and lock into circumferential corneal arch which has prefabricated notches in which the radial corneal arch will be inserted.

Example 18

An arch of Example 2, which is semi-circular in shape, hexagonal in cross section, uniform in cross section. The superior surface of the circumferential arch shall have an interrupted surface. With evenly spaced out recessed carved out of the body of the arch resulting in notches protruding from the superior surface. The arch shall be made of PMMA and can also be made of coloured PMMA.

Example 19

An intra-stromal pattern of sequential radial pockets

Example 20

An intra-stromal incision pattern of Example 19, comprising of individual radial pockets spanning centrally/medially from the limbal area to an area of the central cornea 6mm in diameter.

Example 21

An intra-stromal incision pattern of Example 19, in which the radial incision possess a branch. Allowing for communication of the radial pocket with the anterior corneal surface. Said communicating branch can be 100 to 300 microns in length depending on the depth of the corneal radial pocket. Said communicating branch shall be positioned about 0.5 mm to about 1 mm from the distal end of the radial pocket in relation to the cornea. The communicating branch can be perpendicular or angulated away from the central area towards the lumbus.

Example 22

An intra-stromal incision pattern of Example 19, which comprises of radial pockets numbering from 1 to 16.

Example 23

An intra-stromal incision pattern of Example 19, in which the individual radial pockets are in sagittal view either straight or arched to varying degrees of radius of curvature (6-10 mm) with or against the curvature of the cornea.

Example 24

An intra-stromal incision pattern of Example 19, in which each of the individual pockets are cut either at the same depth or each at varying depths. Depth range is 100 to 300 microns with corresponding change in branch length.

Example 25

An intra-stromal incision pattern of Example 19, in which the position of the radial pockets is either in an evenly distributed manner with equal spacing or varying spacing between them determined by the specific nature of the refractive error.

Example 26

An intra-stromal incision pattern of Example 19, that is to be created by femtosecond laser or by a surgeon created radial/circumferential incisions.

Example 27

An intra-stromal incision pattern of 2 semi-circular pockets that are circumferential and horizontal. The two pockets are interconnected with the radial pockets when in the same plane as the radial pockets of Example 19.

Example 28

An intra-stromal incision pattern of Example 47, to be cut by femtosecond laser technology or by the surgeon with one end of each circumferential arch to be connected to the anterior surface of the cornea.

Example 29

A software programme with the purpose of using intraocular eye pressure and topographical data of a cornea surface from an eye suffering from refractive error and producing an incision pattern and arch combination to assist the surgeon in correct and precise arch implantation to correct the refractive error.

Example 30

A software programme of Example 29 basing its analytics on finite element analysis modelling of the cornea.

Example 31

A software programme of Example 29 using parameters detailing corneal topography and corneal thickness. Such parameters will be used to create a model of the patient's cornea in finite element analysis with consideration of the patient's intra ocular eye pressure. Using said model, a series of corneal arches are inserted within the generated corneal model to illicit the needed changes to the anterior and posterior corneal surface to correct refractive error.

Example 32

A software programme of Example 29 having generated a relevant intrastromal pattern needed for the required corneal curvature change will then export the specific and needed dimensions, depth, number and orientation of the radial and circumferential incisions to a femtosecond laser for incision creation.

Example 33

A software of Example 29 having calculated the correction combination and dimensions of the corneal radial and circumferential arches needed to illicit the corneal shape change need for the surgeon to insert into the femtosecond assisted incisions.

Example 34

A method of treating an eye of a subject comprising forming an incision in a cornea of the eye, and inserting an intra corneal implant into the incision, wherein size of the intra corneal implant and pattern of the incision is determined by consulting a database of treated subjects, wherein the database has been created by recording, for a plurality of prior subjects who had the treatment, one or more of: a baseline corneal radius of curvature, a baseline corneal thickness, a size of intra corneal implant inserted into the eye, the incision pattern used, intraoccular pressure and final corneal radius of curvature (post-treatment). A desired final corneal radius of curvature in an eye can be achieved by measuring a baseline corneal radius of curvature and thickness in the eye of the subject to be treated, consulting the database for the same or similar baseline corneal radii of curvatures, eye thicknesses and/or intraocular pressures, and selecting an implant size and/or pattern to achieve the desired final corneal radius of curvature based on implant size, incision patterns and/or intraocular pressures that achieved a same or similar final corneal radius of curvature in the database of treated subjects.

Example 35

A method of treating an eye of a subject comprising forming an incision in a cornea of the eye, and inserting an intra corneal implant into the incision, wherein size of the intra corneal implant and pattern of incision is determined as a function of one or more of: baseline corneal radius of curvature, baseline corneal thickness, baseline intraoccular pressure and/or final corneal radius of curvature (post-treatment) desired.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

Software includes applications and algorithms. Software may be implemented in a smart phone, tablet, or personal computer, in the cloud, on a wearable device, or other computing or processing device. Software may include logs, journals, tables, games, recordings, communications, SMS messages, Web sites, charts, interactive tools, social networks, VOIP (Voice Over Internet Protocol), e-mails, and videos.

In some embodiments, some or all of the functions or process(es) described herein and performed by a computer program that is formed from computer readable program code and that is embodied in a computer readable medium. The phrase "computer readable program code" includes any type of computer code, including source code, object code, executable code, firmware, software, etc. The phrase "computer readable medium" includes any type of medium capable of being accessed by a computer, such as read only memory (ROM), random access memory (RAM), a hard disk drive, a compact disc (CD), a digital video disc (DVD), or any other type of memory.

What is claimed is:

1. An intracorneal implant comprising:
   a. a peripheral base edge;
   b. a central tip edge;
   c. an arched portion including two generally opposed edges connecting the peripheral base edge and the central tip edge the two generally opposed edges being tapered from the peripheral base edge to the central tip edge in both the cross sectional and sagittal view, wherein the two generally opposed edges extend from the furthest of the peripheral base edge to the furthest of the central tip edge; and
   d. a manipulation hole disposed in the peripheral base edge and traversing a thickness of the peripheral base edge;
   e. the peripheral base edge including a cross-section extending to the central tip edge, wherein the cross section is hexagonal.

2. The intracorneal implant of claim 1, further comprising an overall tapered shape from the peripheral base edge to the central tip edge; wherein the peripheral base edge includes a width and a height greater than a height and a width of the central tip portion.

3. The intracorneal implant of claim 2, wherein the central tip edge includes an upward inflection towards the anterior corneal surface, or a downwards inflection towards the posterior corneal surface.

4. The intracorneal implant of claim 1, wherein the central tip edge and the peripheral base edge are flat with respect to the central optical zone of the cornea, or the central tip edge and the peripheral base edge are curved away from the central optical zone of the cornea.

5. The intracorneal implant of claim 1, wherein the implant is made from a substantially rigid material with clarity up to 100% and no less than 60% to allow light to transverse through the implant unhindered or undeflected.

6. The intracorneal implant of claim 5, wherein the implant material is of the same refractive index as the cornea.

7. The intra corneal implant of claim 5, wherein the curved edge is curved inwardly.

8. An intracorneal implant of claim 1 comprising;
   a. A Circumferentially planar shape;
   b. A Inner arched edge;
   c. A Outer arched edge;
   d. A Smooth inferior surface;
   e. A Notched superior surface, wherein the notched superior surface includes a plurality of notches sized and shaped to interact with the two generally opposed edges of the corneal implant of claim 1; and
   f. The plurality of notches on the superior surfaces include tapered edges for interacting with the tapered edges of the corneal implant of claim 1.

9. The implant of claim 1, peripheral base edge including a cross-section extending to the central tip edge, wherein the cross section is rectangular or oval shaped.

10. The implant of claim 1, wherein implant is made from a biocompatible material, synthetic collagen, or a collagen material.

11. The intra corneal implant of claim 1, wherein the peripheral base edge is curved.

12. The intra corneal implant of claim 1, wherein the peripheral base edge is curved outwardly.

13. The intra corneal implant of claim 1, wherein the central tip edge comprises a curved edge.

14. The intra corneal implant of claim 1, wherein the arched portion has a radius of curvature of about 6 mm to about 10 mm.

15. The intra corneal implant of claim 1, wherein the intra corneal implant has a length of about 1.5 mm to about 5 mm, a width of about 0.25 mm to about 2.5 mm, and a cross sectional thickness of about 50 microns to about 300 microns.

16. The intra corneal implant of claim 1, wherein the arched portion includes a peripheral edge.

17. An intracorneal implant comprising:
   a. a peripheral base edge;
   b. a central tip edge;
   c. an arched portion including two generally opposed edges connecting the peripheral base edge and the central tip edge the two generally opposed edges being tapered from the peripheral base edge to the central tip edge in both the cross sectional and sagittal view, wherein the two generally opposed edges extend from the furthest of the peripheral base edge to the furthest of the central tip edge, and the two generally opposed edges are continuous from a top portion of the arched portion to a bottom portion of the arched portion;
   d. a manipulation hole disposed in the peripheral base edge and traversing a thickness of the peripheral base edge;
   e. the peripheral base edge including a cross-section extending to the central tip edge, wherein the cross section is hexagonal.

18. An intracorneal implant comprising:
   a. a peripheral base edge;
   b. a central tip edge;
   c. an arched portion including two generally opposed edges connecting the peripheral base edge and the central tip edge the two generally opposed edges being tapered from the peripheral base edge to the central tip edge in both the cross sectional and sagittal view, wherein the two generally opposed edges extend from the furthest of the peripheral base edge to the furthest of the central tip edge, and the two generally opposed edges are continuous from a top portion of the arched portion to a bottom portion of the arched portion;
d. a manipulation hole disposed in the peripheral base edge and traversing a thickness of the peripheral base edge, and the manipulation hole traverses a width of the peripheral base edge;
e. the peripheral base edge including a cross-section extending to the central tip edge, wherein the cross section is hexagonal.

19. The implant of claim 18, peripheral base edge including a cross-section extending to the central tip edge, wherein the cross section is rectangular or oval shaped.

20. The implant of claim 18, wherein implant is made from a biocompatible material, synthetic collagen, or a collagen material.

\* \* \* \* \*